United States Patent
Johnson et al.

(10) Patent No.: US 10,634,609 B2
(45) Date of Patent: Apr. 28, 2020

(54) SENSOR SYSTEM FOR MEASURING A SNOWPACK PROFILE

(71) Applicant: Realtime Adventure Data, Inc., Boise, ID (US)

(72) Inventors: Micah J. Johnson, Boise, ID (US); Ryan Stevenson, Boise, ID (US); Drew Eldred, Boise, ID (US)

(73) Assignee: REALTIME ADVENTURE DATA, INC., Boise, ID (US)

( * ) Notice: Subject to any disclaimer, the term of this patent is extended or adjusted under 35 U.S.C. 154(b) by 183 days.

(21) Appl. No.: 15/760,223

(22) PCT Filed: Sep. 28, 2016

(86) PCT No.: PCT/US2016/054203
§ 371 (c)(1),
(2) Date: Mar. 14, 2018

(87) PCT Pub. No.: WO2017/058929
PCT Pub. Date: Apr. 6, 2017

(65) Prior Publication Data
US 2018/0259447 A1    Sep. 13, 2018

Related U.S. Application Data

(60) Provisional application No. 62/234,350, filed on Sep. 29, 2015.

(51) Int. Cl.
*G01N 21/3563* (2014.01)
*G01N 3/00* (2006.01)
(Continued)

(52) U.S. Cl.
CPC ......... *G01N 21/3563* (2013.01); *E02D 1/022* (2013.01); *G01N 3/00* (2013.01);
(Continued)

(58) Field of Classification Search
CPC .... G01N 21/3563; G01N 3/00; G01N 21/474; G01N 33/18; G01N 2021/0118;
(Continued)

(56) References Cited

U.S. PATENT DOCUMENTS 9,057,803 B2 *  6/2015  Christian ............... G01W 1/14
9,465,020 B2 * 10/2016  Christian ............... G01W 1/14
(Continued)

FOREIGN PATENT DOCUMENTS

RU        2262718       10/2005
WO   WO-2014124332 A2   2/2014

*Primary Examiner* — David P Porta
*Assistant Examiner* — Meenakshi S Sahu
(74) *Attorney, Agent, or Firm* — Your Intellectual Property Matters, LLC; Robert A. Frohwerk

(57) ABSTRACT

A sensor system is for measuring the profile of a snowpack along a snowpack passage. The sensor system has a probe and at least one processor. The probe has at least one first sensor set. The first sensor set has at least one first photoemitter for emitting light and at least one first photodetector for detecting light. A processor is provided for receiving output signals from the first sensor set. The processor is for calculating a snowpack profile.

20 Claims, 11 Drawing Sheets

(51) Int. Cl.
| | |
|---|---|
| *E02D 1/02* | (2006.01) |
| *G01W 1/14* | (2006.01) |
| *G01N 21/47* | (2006.01) |
| *G01N 33/18* | (2006.01) |
| *G01W 1/10* | (2006.01) |
| *G01N 21/01* | (2006.01) |

(52) U.S. Cl.
CPC ........... *G01N 21/474* (2013.01); *G01N 33/18* (2013.01); *G01W 1/10* (2013.01); *G01W 1/14* (2013.01); *G01N 2021/0118* (2013.01); *G01N 2021/0125* (2013.01); *G01N 2021/4709* (2013.01); *G01N 2021/4742* (2013.01); *G01N 2033/1873* (2013.01)

(58) Field of Classification Search
CPC ... G01N 2021/0125; G01N 2021/4709; G01N 2021/4742; G01N 2033/1873; G01N 9/00; G01N 3/08; G01N 3/60; G01N 11/10; G01N 17/00; G01N 3/42; G01N 2203/0082; G01N 19/00; E02D 1/022; G01W 1/14; G01W 1/10; G01B 11/14; G01B 5/30; G01B 21/18; G01B 7/26; G08C 17/02
See application file for complete search history.

(56) References Cited

U.S. PATENT DOCUMENTS

| | | |
|---|---|---|
| 2009/0103091 A1 | 4/2009 | Jones et al. |
| 2011/0261350 A1 | 10/2011 | Jung et al. |
| 2014/0366648 A1 | 12/2014 | Christian et al. |

* cited by examiner

SENSOR SYSTEM FOR MEASURING A SNOWPACK PROFILE

TECHNICAL FIELD

The disclosure generally relates to the field of sensor systems. Particular embodiments relate to sensor systems for measuring the profile of a snowpack and assessing avalanche risk.

BACKGROUND

Information on structure and stability of a snowpack in a given area is essential to assess avalanche conditions. Because certain geographic areas are often inaccessible, snowpack properties can be estimated by analyzing past and present avalanche events. However, such characteristics can vary greatly over time and geographical regions, making snowpack characteristics difficult to assess.

SUMMARY OF THE DISCLOSURE

Several exemplary sensor systems are described herein.

An exemplary sensor system is for measuring the profile of a snowpack along a snowpack passage, said sensor system comprising: a probe and at least one processor; said probe comprising a probe tip for insertion into said snowpack; said probe comprising at least one first sensor set, said first sensor set comprising at least one first photoemitter and at least one first photodetector, said at least one first photoemitter for emitting a first light signal towards and into said snowpack passage at a first sensor set port, said at least one first photodetector at a second sensor set port for detecting the intensities of said first light signal reflected back from said snowpack passage, said first sensor set generating a first output signal related to light intensity detected by said at least one first photodetector, said probe generating a second output signal related to the speed at which the probe moved through the snowpack; and said at least one processor for implementing processor functions in response to receiving said first output signal and said second output signal, said processor functions including: executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile.

Another exemplary sensor system is for measuring the profile of a snowpack along a snowpack passage, said sensor system comprising: a probe and at least one processor; said probe comprising a probe tip for insertion into said snowpack; said probe comprising at least one first sensor set, said first sensor set comprising at least one first photoemitter and at least one first photodetector, said at least one first photoemitter for emitting a first light signal towards and into said snowpack passage at a first sensor set port, wherein said at least one first photoemitter emits infrared light, wherein said at least one first photodetector detects infrared light, said at least one first photodetector at a second sensor set port for detecting the intensities of said first light signal reflected back from said snowpack passage, said first sensor set port and said second sensor set port are located proximal to said probe tip, wherein said at least one first photoemitter and said at least one first photodetector of said at least one sensor set is located distally from said probe tip, said first sensor set generating a first output signal related to light intensity detected by said at least one first photodetector, said probe generating a second output signal related to the speed at which the probe moved through the snowpack, wherein said probe further comprises a barometer, and wherein the second output signal is generated by said barometer; said at least one processor for implementing processor functions in response to receiving said first output signal and said second output signal, said processor functions including: executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile; wherein said at least one sensor set further comprises at least one first optical fiber for transferring light from said at least one photoemitter to at least one photoemitter port, and at least one second optical fiber for transferring light from at least one photodetector port to said at least one photodetector, wherein said first sensor set port comprises said at least one photoemitter port, and wherein said second sensor set port comprises said at least one photodetector port.

Additional understanding of the devices and methods contemplated and/or claimed by the inventors can be gained by reviewing the detailed description of exemplary devices and methods, presented below, and the referenced drawings.

DEFINITIONS

Figure 1:
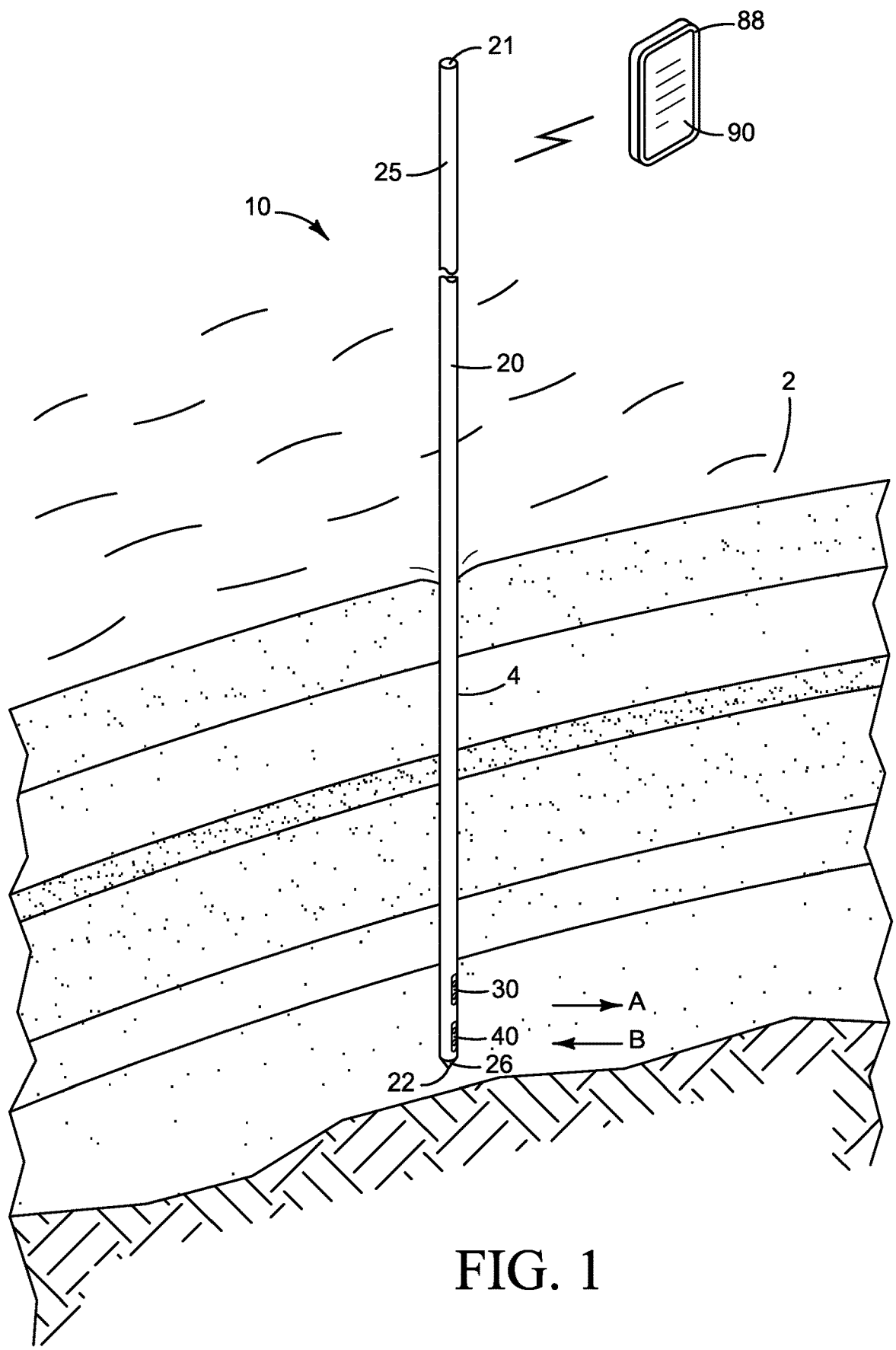
FIG. 1 is an environmental, perspective view of a first exemplary sensor system.
Figure 2:
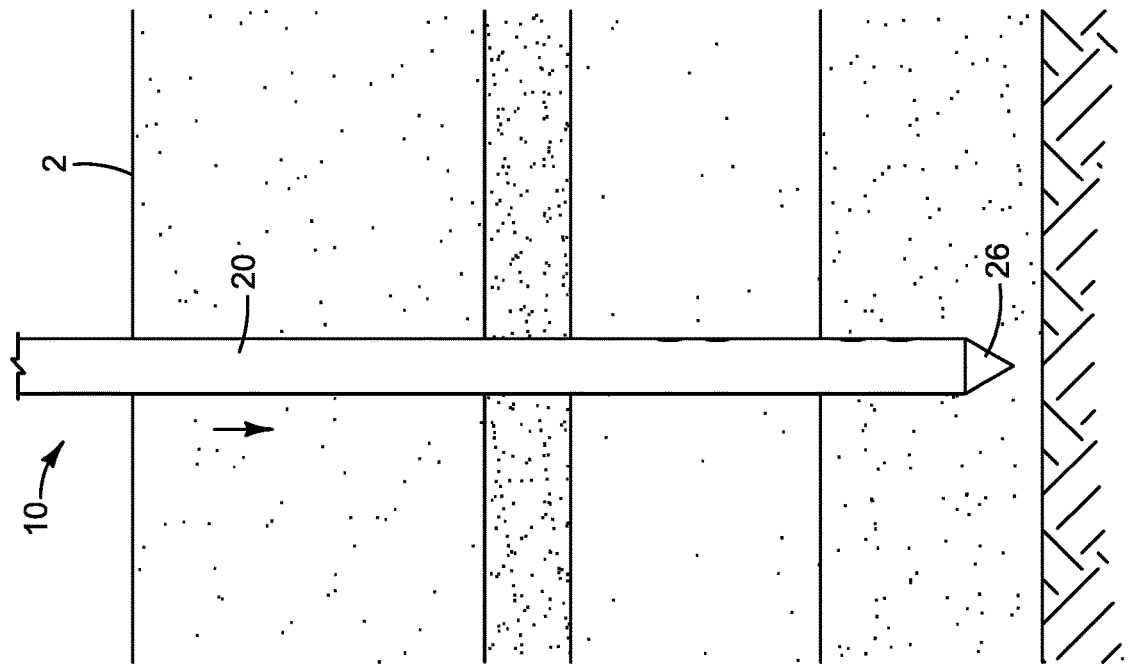
FIG. 2 is an environmental, side view of the first exemplary sensor system.
Figure 3:
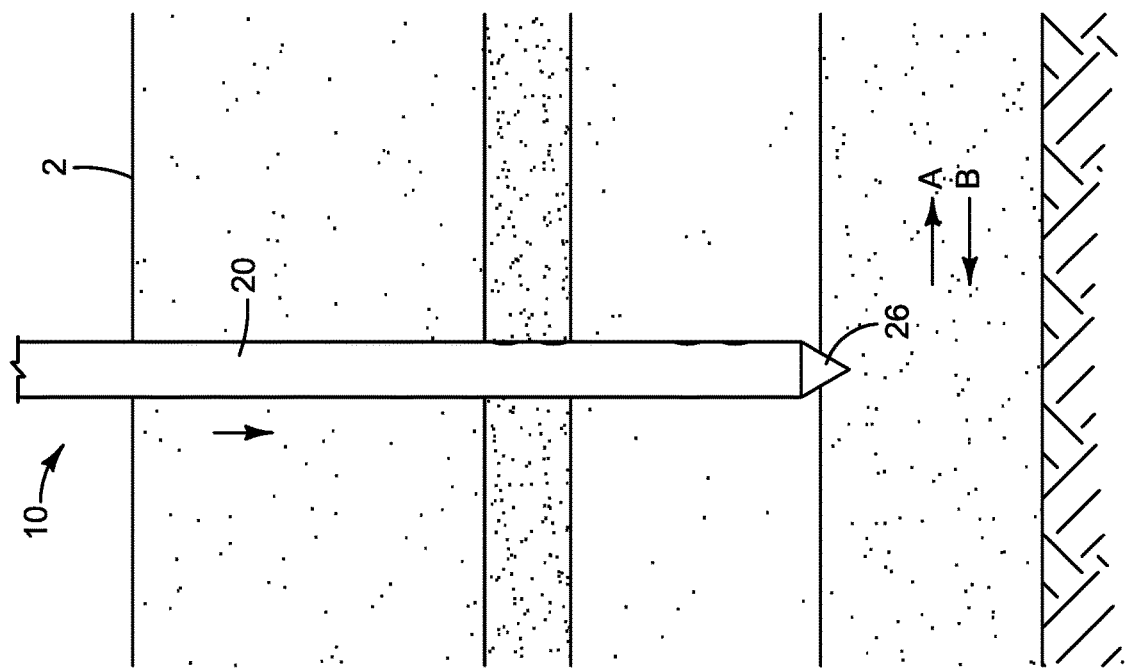
FIG. 3 is an environmental, side view of the first exemplary sensor system.
Figure 4A:
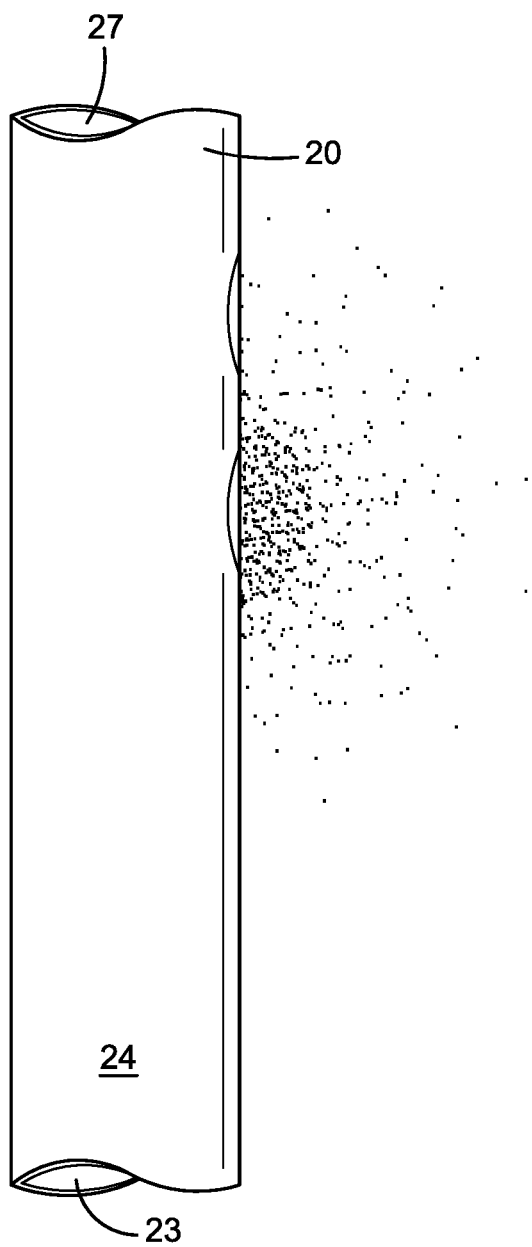
FIG. 4A is an environmental, side view of the first exemplary sensor system.
Figure 4B:
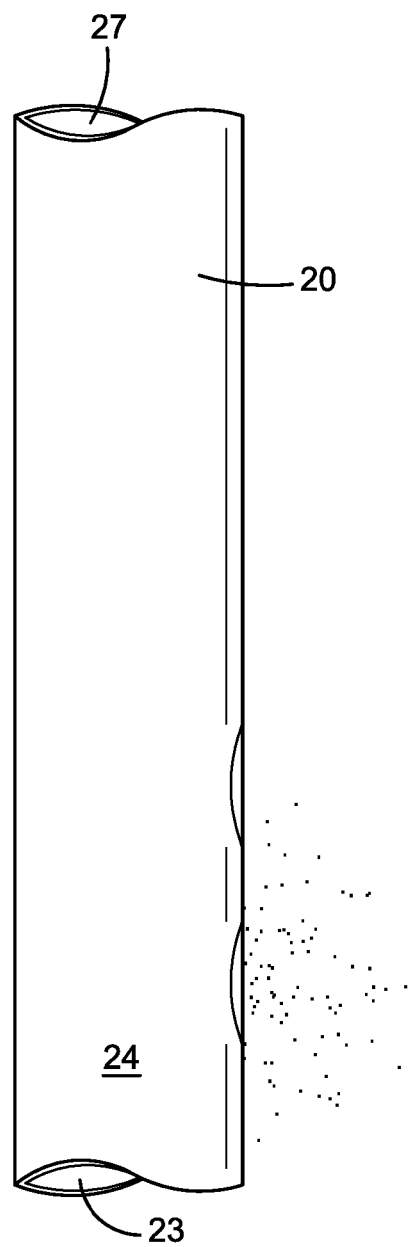
FIG. 4B is an environmental, side view of the first exemplary sensor system.
Figure 5:
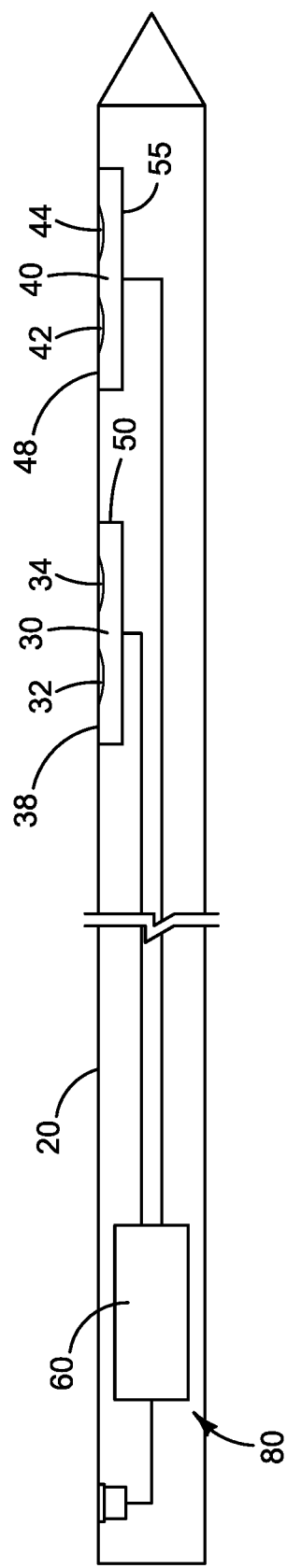
FIG. 5 is a schematic representation of the first exemplary sensor system of FIG. 1.
Figure 6:
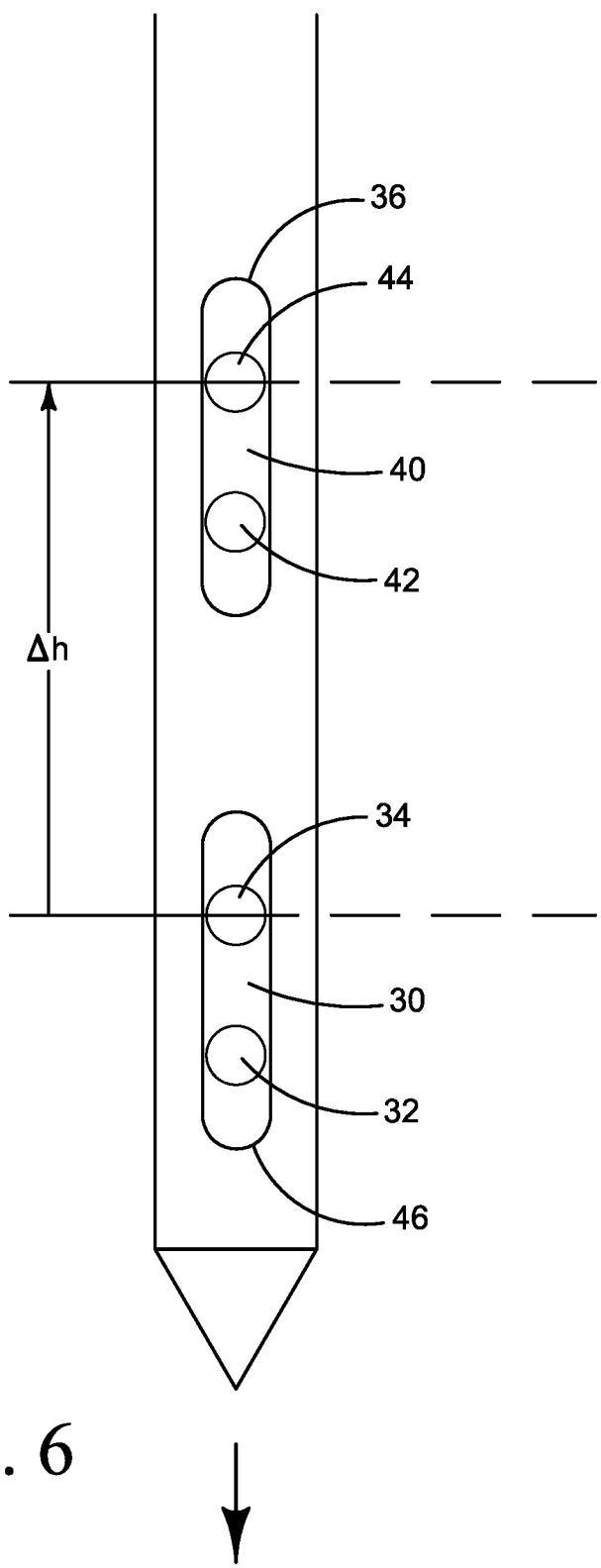
FIG. 6 is a partial, side schematic representation of the first exemplary sensor system.

The use of "e.g.," "etc," "for instance," "in example," "for example," and "or" and grammatically related terms indicates non-exclusive alternatives without limitation, unless the context clearly dictates otherwise. The use of "including" and grammatically related terms means "including, but not limited to," unless the context clearly dictates otherwise. The use of the articles "a," "an" and "the" are meant to be interpreted as referring to the singular as well as the plural, unless the context clearly dictates otherwise. Thus, for example, reference to "a sensor" includes two or more such sensors, and the like. The use of "optionally," "alternatively," and grammatically related terms means that the subsequently described element, event or circumstance may or may not be present/occur, and that the description includes instances where the element, event or circumstance occurs and instances where it does not. The use of "preferred," "preferably," and grammatically related terms means that a specified element or technique is more acceptable than another, but not that such specified element or technique is a necessity, unless the context clearly dictates otherwise. The use of "exemplary" means "an example of" and is not intended to convey a meaning of an ideal or preferred embodiment. Words of approximation (e.g., "substantially," "generally"), as used in context of the specification and figures, are intended to take on their ordinary and customary meanings which denote approximation, unless the context clearly dictates otherwise.

The use of "probe" means a device, typically of rod shape, suitable for insertion into a snowpack, unless the context clearly dictates otherwise. One example of a probe is a ski pole.

The use of "photoemitter" means any device for emitting photoelectrons (e.g., infra-red light, ultra-violet light), either visible or invisible, that is capable of being detected, unless the context clearly indicates otherwise. Examples of photoemitters include, but are not limited to, electroluminescent lamps (e.g., light-emitting diodes (LEDs), electroluminescent paint, and electroluminescent wires).

The use of "light-emitting diode" means a semiconductor diode that emits light when a voltage is applied to it, unless the context clearly indicates otherwise.

The use of "photodetector" means any device that is capable of detecting the presence of, absence of, and/or a change in the intensity of any kind of radiation beam, and outputting signal information related thereto, unless the context clearly dictates otherwise. Examples of photodetectors include, but are not limited to, image sensors, charge-coupled devices, HgCdTe infrared detectors, light-emitting diodes (LEDs) which are reverse-biased to act as photodiodes, optical detectors, photoresistors, photovoltaic cells, photodiodes, barometers, accelerometers, infrared range finders, and altimeters.

The use of "energy storage system" means a system that stores electrical energy for powering an electrical device, including but not limited to batteries, rechargeable batteries, capacitors, ultracapacitors, and combinations thereof, unless the context clearly indicates otherwise.

The use of "control system" means any type of device for controlling the operation of one or more components of a sensor system for measuring a snowpack profile and assessing avalanche risk, unless the context clearly indicates otherwise.

The use of "processor" means a programmable analog and/or digital device that can store, retrieve, and process data; a handheld computing device (e.g., a mobile phone, a tablet computer); a computer; a microprocessor; a microcontroller; a microcomputer; or any suitable processing device or apparatus, unless the context clearly dictates otherwise.

The use of "user interface" means any device for rendering information to a user and/or requesting information from the user, including but not limited to a digital screen, monitor, display, visual indication device (such as a light), and an audio element emitted from a speaker, unless the context clearly dictates otherwise.

The use of "sensor" means a device that detects events or changes in quantities and provides a corresponding output, generally as an electrical or optical signal, unless the context clearly indicates otherwise. Examples of sensors include, but are not limited to: acoustic sensors, vibration sensors, electrical sensor, electric current sensors, electric potential sensors, magnetic sensors, radio sensors, environmental sensors, moisture sensors, humidity sensors, motion sensors, position sensors, angle sensors, displacement sensors, distance sensors, speed sensors, acceleration sensors, electro-optical sensors, pressure sensors, thermal sensors, and proximity sensors.

The use of "speed" means the velocity or rate of motion of the probe relative to the snowpack, unless the context clearly dictates otherwise.

The use of "snowpack" means a mass of snow on a ground surface, unless the context clearly dictates otherwise.

The use of "snowpack profile" means a profile of the layers of a snowpack, unless the context clearly dictates otherwise.

The use of "snowpack passage" means a path through a snowpack, preferably linear, unless the context clearly dictates otherwise.

DETAILED DESCRIPTION

The following description and the referenced drawings provide illustrative examples of that which the inventors regard as their invention. As such, the embodiments discussed herein are merely exemplary in nature and are not intended to limit the scope of the invention, or its protection, in any manner. Rather, the description and illustration of these embodiments serve to enable a person of ordinary skill in the relevant art to practice the invention.

Disclosed are exemplary sensor systems for measuring a snowpack profile and assessing avalanche risk.

FIGS. 1 through 6 illustrate a first exemplary sensor system 10 for measuring the profile of a snowpack along a snowpack passage 4 and assessing avalanche risk.

The first exemplary sensor system 10 comprises a probe 20 that has an inner wall 23 and outer wall 24. The inner wall 23 and outer wall 24 extend from a first end 21 to a second end 22. The second end 22 comprises a probe tip 26 for insertion into a snowpack 2. Preferably, the probe 20 is generally cylindrical in shape, such that the inner wall 23 and outer wall 24 form a cavity 27. Preferably, the cavity extends from the first end 21 to the second end 22, which allows components to be housed therein. The first end 21 of the probe 20 comprises a handle portion 25. Preferably, the handle portion 25 contains the control system 80 of the first exemplary sensor system for measuring the profile of a snowpack 2. Optionally, however, the control system 80 can be contained elsewhere, such as in an external electronic device 88.

The handle portion 25 serves as point for a user to grasp when he or she inserts the first exemplary sensor system 10 into a snowpack 2. For example, the handle portion can comprise a grip that gives the user extra stability when he or she exerts a force upon the probe.

The probe tip 26 is the leading edge of the probe 20, and is preferably configured for minimal resistance when the probe tip 26 penetrates a snowpack 2. The probe tip 26 is preferably an aluminum cylinder that is press-fit into the second end 22 of the probe 20, however a skilled artisan will be able to select an appropriate structure and material for the probe 20 and probe tip 26 in a particular embodiment based on various considerations, including the intended use of the probe 20 and probe tip 26, the intended arena within which the probe 20 and probe tip 26 will be used, and the equipment and/or accessories with which the probe 20 and probe tip 26 are intended to be used, among other considerations. Preferably, the probe tip 26 has a generally conical shape. Alternatively, the shape of the probe tip 26 can be altered without any change in functionality, perhaps even performance enhancing benefits, for instance through the use of a sharpened or rectangular tip has help to reduce the alteration of the snowpack 2 as the probe penetrates.

When not in use, a tip cover (not illustrated) can be placed over the probe tip 26 to protect the probe tip 26 from damage when not in use. Alternatively, basket or other structure could be added to the probe 20, near the probe tip 26, to limit the insertion of the probe tip 26 into the snowpack 2 when the embodiments of the exemplary sensor systems are not in use.

The first exemplary sensor system 10 further comprises at least one first sensor set 30 and at least one second sensor set 40 configured to detect variations in the characteristics within a snowpack and to provide a corresponding data output to a processor 60 which calculates a snowpack profile. In the first exemplary sensor system 10, the first sensor set 30 comprises at least one first photoemitter 32 and at least one first photodetector 34. The first photoemitter 32 configured for emitting a first light signal towards and into the snowpack 2, and the at least one first photodetector 34 configured to detect the intensity of the first light signal reflected back from the snowpack 2 in a snowpack passage 4 and to output a first output signal related to light intensity detected by the at least one first photodetector 34.

Preferably, the first photoemitter 32 emits infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the first photoemitter 32 could emit visible and/or ultraviolet light in addition to, or instead of, infrared light.

The first photodetector 34 is configured for sensing light emitted from the first photoemitter 32 which has reflected off a snowpack 2 in a snowpack passage 4. In that the preferred first photoemitter 32 emits infrared light, the first photodetector 34 is configured for sensing infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the first photodetector 34 could detect visible and/or ultraviolet light in addition to, or instead of, infrared light.

In the exemplary sensor system 10, the first photoemitter 32 is configured to emit a first light signal in first direction A. The first direction A preferably represents radiating generally outwards from the first photoemitter 32. A skilled artisan will be able to select an appropriate direction or directions of radiation in a particular embodiment based on various considerations, including the intended use of the sensory system, the intended arena within which the sensory system will be used, and the equipment and/or accessories with which the sensory system is intended to be used, among other considerations. For instance, the first direction A could be generally towards the first photodetector 34.

When the first exemplary sensor system 10 is inserted into the snowpack 2 and moved along a snowpack passage 4, the first light signal is emitted into the snowpack 2, and the first photodetector 34 detects the first light signal.

The first photodetector 34 generates a first output signal related to the intensity of the first light signal reflected off the snowpack 2 in a snowpack passage 4 and back to the first photodetector 34. This first output signal is then transferred to the processor 60. For instance, the first output signal can be transferred to the processor 60 by electrical wiring that connects the processor 60 to the first photodetector 34. Alternatively, the first output signal can be transferred to the processor 60 by a transmitter connected to the first photodetector 34, which transmits the first output signal to a receiver connected to the processor 60. Further alternatively, the first output signal can be transferred to the processor 60 by optical fibers (aka, fiber optics), by mirrors, by prisms, etc. A skilled artisan will be able to select an appropriate mechanism for transferring the first output signal to the processor 60 in a particular embodiment based on various considerations, including the arena within which the sensor system will take place and the equipment and/or accessories with which the sensor system 10 will be used, among other considerations.

While the exemplary sensor system 10 illustrated in these drawings shows a single first photoemitter 32 and a single first photodetector 34, a single photoemitter can be used with a plurality of photodetectors, a single photodetector could be utilized with a plurality of photoemitters, and various combinations of the same could be used. For example, a photoemitter can be surrounded by a plurality of photodetectors in which the photoemitter emits light in a first direction. When the light reflects off a snowpack and returns in a second direction, the plurality of photodetectors receives the light and, in turn, generates a plurality of output data. This output data is then received by the processor, in the same manner as with a single photodetector. A skilled artisan will be able to select an appropriate number of photodetectors and photoemitters for an exemplary sensor system in a particular embodiment based on various considerations, including the intended use of the sensor system, the intended arena within which the sensor system will be used, and the equipment and/or accessories with which the sensor system is intended to be used, among other considerations.

The first exemplary sensor system 10 further comprises a second sensor set 40 comprising at least one second photoemitter 42 and at least one second photodetector 44. The second photoemitter 42 emits a second light signal towards and into the snowpack 2 such that the second photodetector 44 can detect the intensity of the second light signal reflected back from the snowpack 2 in a snowpack passage 4 and generate a second output signal related to the speed at which the probe moved through the snowpack. In the first exemplary sensor system 10, the second output signal is more specifically related to light intensity detected by the second photodetector 44.

Preferably, the second photoemitter 42 emits infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the second photoemitter 42 could emit visible and/or ultraviolet light in addition to, or instead of, infrared light.

The second photodetector 44 is configured for sensing light emitted from the second photoemitter 42 which has reflected off a snowpack 2 in a snowpack passage 4. In that the preferred second photoemitter 42 emits infrared light, the second photodetector 44 is configured for sensing infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the second photodetector 44 could detect visible and/or ultraviolet light in addition to, or instead of, infrared light.

In the exemplary sensor system 10 of FIGS. 1 through 6, the second sensor set 40 comprises at least one second photoemitter 42 and at least one second photodetector 44. The second photoemitter 42 is configured to emit a second light signal towards and into the snowpack 2, and the at least one second photodetector 44 is configured to detect the intensity of the second light signal reflected back from the snowpack 2 in a snowpack passage 4 and to output a second output signal related to light intensity detected by the at least one second photodetector 44. This second output signal is transferred to the processor 60.

The second photoemitter 42 is configured for emitting a second light signal in the first direction A. The first direction A preferably represents radiating generally outwards from the second photoemitter 42. A skilled artisan will be able to select an appropriate direction or directions of radiation in a particular embodiment based on various considerations, including the intended use of the sensory system, the intended arena within which the sensory system will be used, and the equipment and/or accessories with which the sensory system is intended to be used, among other considerations. For instance, the first direction A could be generally towards the second photodetector 44.

When the first exemplary sensor system 10 is inserted into the snowpack 2 along a snowpack passage 4, the second light signal is emitted into the snowpack 2, and the second photodetector 44 detects the second light signal.

The sensor sets (30, 40) are configured to detect variations in the characteristics of a snowpack and to provide corresponding data output to the processor 60. Once the processor 60 receives the data received and from the sensor sets (30, 40), the data can be processed into a snowpack profile that is presented to a user. In one example, the sensor sets (30, 40) could measure reflectance of the profile of the snowpack to create a data output to the processor. The processor could then correlate the measured reflectance to density, and present the correlated density to the user as a density profile for the snowpack. In other examples, other characteristics of a snowpack could be utilized. For instance, snow water equivalent, snowpack temperature, snowpack stability, and albedo.

While the exemplary sensor system 10 illustrated in these drawings shows a single second photoemitter 42 and a single second photodetector 44, a single photoemitter can be used with a plurality of photodetectors, a single photodetector could be utilized with a plurality of photoemitters, and various combinations of the same could be used. For example, a photoemitter can be surrounded by a plurality of photodetectors in which the photoemitter emits light in a first direction. When the light reflects off a snowpack and returns in a second direction, the plurality of photodetectors receives the light and, in turn, generates a plurality of output data. For instance, the plurality of sensors could characterize the shape of the snow grains found in the snowpack (e.g., spatial averaging, grain size) as part of generating a plurality of data output.

This output data is then received by the processor, in the same manner as with a single photodetector. A skilled artisan will be able to select an appropriate number of photodetectors and photoemitters for an exemplary sensor system in a particular embodiment based on various considerations, including the intended use of the sensor system, the intended arena within which the sensor system will be used, and the equipment and/or accessories with which the sensor system is intended to be used, among other considerations.

The second output signal related to light intensity detected by the at least one second photodetector 44 is then transferred to the at least one processor 60. For instance, the second output signal can be transferred to the processor 60 by electrical wiring connecting the processor 60 to the second photodetector 44. Alternatively, the second output signal can be transferred to the processor 60 by a transmitter connected to the second photodetector 44, which transmits the second output signal to a receiver connected to the processor 60. Further alternatively, the second output signal can be transferred to the processor 60 by optical fibers (aka, fiber optics). A skilled artisan will be able to select an appropriate mechanism for transferring the first output signal to the processor 60 in a particular embodiment based on various considerations, including the arena within which the sensor system will take place and the equipment and/or accessories with which the sensor system 10 will be used, among other considerations.

The first sensor set 30 and the second sensor set 40 are mounted or otherwise attached to the probe 20. In the exemplary sensor system 10 illustrated in these Figures, the probe 20 comprises a first sensor mount 50 to which the first sensor set 30 can be mounted, and a second sensor mount 55 to which the second sensor set 40 can be mounted. The first sensor mount 50 is attached to the inner wall 23 of the probe 20, adjacent the probe tip 26. The second sensor mount 55 is attached to the inner wall 23 of the probe 20 more distal from the probe tip 26 than the first sensor mount 50. Alternatively, the first sensor mount 50 could not be adjacent the probe tip 26.

The first sensor mount 50 and the second sensor mount 55 for holding the first sensor set 30 and second sensor set 40 in a fixed, generally linear, position. Preferably, the first sensor mount 50 and the second sensor mount 55 are each machined into the inner wall 23 and match the general dimensions of the first sensor set 30 and second sensor set 40. When inserted into the first sensor mount 50 and the second sensor mount 55 in fixed positions, the first light signal emitted from the first photoemitter 32 and second light signal emitted from the second photoemitter 42 extend in a generally parallel manner.

Also adjacent the probe tip 26 is a first sensor viewport 36 and second sensor viewport 46. These viewports extend through both the inner wall 23 and outer wall 24, which allows the first photoemitter 32 and second photoemitter 42 to emit a first light signal and second light signal in a first direction A. Additionally, the first sensor viewport 36 and second sensor viewport 46 allow the first photodetector 34 and second photodetector 44 to receive deflected light traveling in a second direction B.

Preferably, the first sensor viewport 36 and second sensor viewport 46 are covered, respectively, by a first sensor viewport cover 38 and second sensor viewport cover 48. These viewport coverings allow for the transmission of light therethrough, and are made of any plastic that allows light to freely pass therethrough. Alternatively, the first and/or second sensor viewport covers could be covered with hydrophobic coating to reduce water accumulation and therefore decreasing distortion of the light signal(s). Alternatively, the first sensor viewport 36 and second sensor viewport 46 can be made of a light filtering material, for instance acrylic plastic. Such a material is incorporated to accommodate filtering undesired wavelengths of light.

The processor 60 is configured to receive data corresponding to the first output signal and second output signal. The processor 60 is preferably located within the cavity 27 created within the probe by the inner wall 23 and outer wall 24. However, the processor can also be located exterior the cavity 27, thus a skilled artisan will be able to select an appropriate structure and location for the processor 60 in a particular embodiment based on various considerations, including the intended use of the processor 60, the intended arena within which the processor 60 will be used, and the equipment and/or accessories with which the processor 60 is intended to be used, among other considerations.

In the exemplary sensor system 10 the processor 60 preferably executes at least three algorithms to determine the snowpack profile.

The first algorithm processes the first output signal to calculate a light intensity profile.

The second algorithm processes the second output signal relative to the first output signal to calculate a speed profile. The speed profile represents the relative movement of the probe 20 as it is moved along the snowpack 2. In one exemplary second algorithm, the speed profile is calculated by first gathering data from the first sensor set 30 and second sensor set 40 as the probe 20 is inserted into a snowpack 2. The data collected by the first sensor set 30 and second sensor set 40 is normalized by the respective max value of each sensor. Using the primary signal of the first sensor set 30 and second sensor set 40, a finite number of unique maximum values are located within the snowpack 2. Using a correlation, the unique maximum values are compared with the respective maximum value of each sensor, resulting in a time difference between primary features. Once this time difference has been calculated, velocity of the probe 20 is calculated by dividing the distance between the first sensor set 30 and second sensor set 40 by the time difference; the distance between the first sensor set 30 and second sensor set 40 is a fixed (illustrated as Δh in FIG. 6), known value. Because velocity is not known for every point within the snowpack 2, velocity is estimated for these points by interpolating between the known velocities, while assuming zero velocity when the probe 20 is at rest.

The third algorithm processes the light intensity profile in view of the speed profile to create a snowpack profile. Preferably, the snowpack profile is displayed on a display 90 for the user to view. Preferably, the display 90 is located on the probe 20 of the first exemplary sensor system 10 such that a user can readily view it. However, the display 90 can be located external the probe 20 in a sensor system 10 such as a computer, PDA, or cellular phone. Again, a skilled artisan will be able to select an appropriate structure and material for the display 90 in a particular embodiment based on various considerations, including the intended use of the display 90, the intended arena within which the display 90 will be used, and the equipment and/or accessories with which the display 90 is intended to be used, among other considerations.

To measure a snowpack profile, the first exemplary sensor system 10 is inserted into a snowpack 2 along a snowpack passage 4. The depth of the probe 20 is calculated using the emitted light and light intensity. Specifically, the light emitted from the first photoemitter 32 and second photoemitter 42 reflects off the snowpack 2 and is then measured by the first photodetector 34 and second photodetector 44. The processor 60 then analyzes the similarity in the measurements collected by the first photodetector 34 and second photodetector 44 as they pass the same point and calculates probe depth based on the time between these similar readings.

As the probe 20 is inserted into the snowpack 2 in a generally linear manner, the snowpack properties are measured transversely. By measuring transversely, more accurate measurements can be achieved by measuring the undisturbed snow adjacent to the path of the probe (along a snowpack passage). This is opposed to measuring oncoming, damaged snow, damaged by the probe 20 sliding through the snowpack passage 4.

By measuring the amount of light that is reflected off, or transmitted through, a snowpack 2 in a snowpack passage 4, the first exemplary sensor system 10 can calculate a snowpack profile. Further, the configuration of the first photoemitter 32 and second photoemitter 42 can be used to measure snow properties in-situ with minimal impact on the snow structure. The first exemplary sensor system 10 thus measures the albedo, refraction, and transparency of the layers in the snowpack along the snowpack passage, to which properties of the snowpack can be correlated.

The first exemplary sensor system 10 can send measurements to a mobile device via a wireless transmission technology such as Bluetooth low energy. The mobile device can then process the data and upload it directly to a server, which hosts a web platform for users to view the data.

Figure 7A:
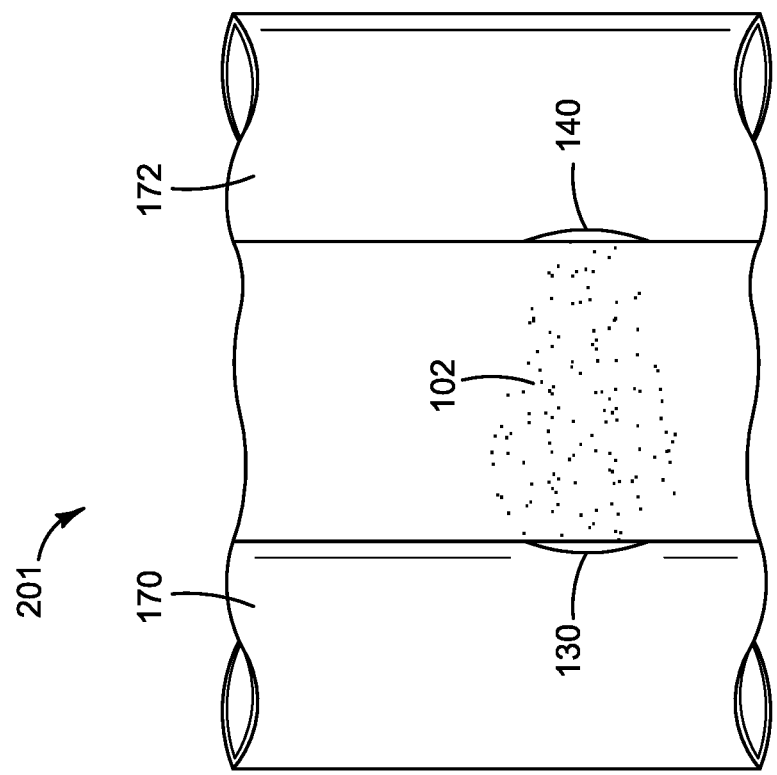
FIG. 7A is an environmental, side view of a second exemplary sensor system.
Figure 7B:
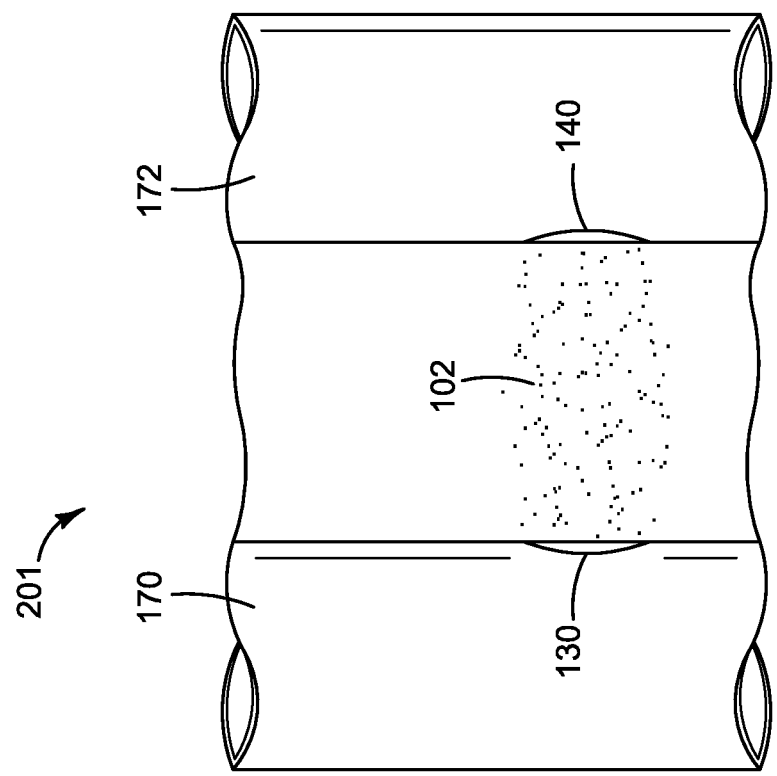
FIG. 7B is an environmental, side view of the second exemplary sensor system of FIG. 7A.

Referring now to FIGS. 7A and 7B, a second exemplary sensor system 201 is illustrated. The second exemplary sensor system 201 is similar to the first exemplary sensor system 10 illustrated in FIGS. 1 through 6 and described above, except as detailed below. Thus, the second exemplary sensor system 201 includes a probe comprising a first prong 170 and second prong 172. When inserted into the snowpack 102, the first sensor set 130 and second sensor set 140 measure the light transmittance of the snowpack 102 between the first prong 170 and second prong 172. The distance between the first prong 170 and second prong 172 can be altered based on the most accurate measurements.

Figure 8:
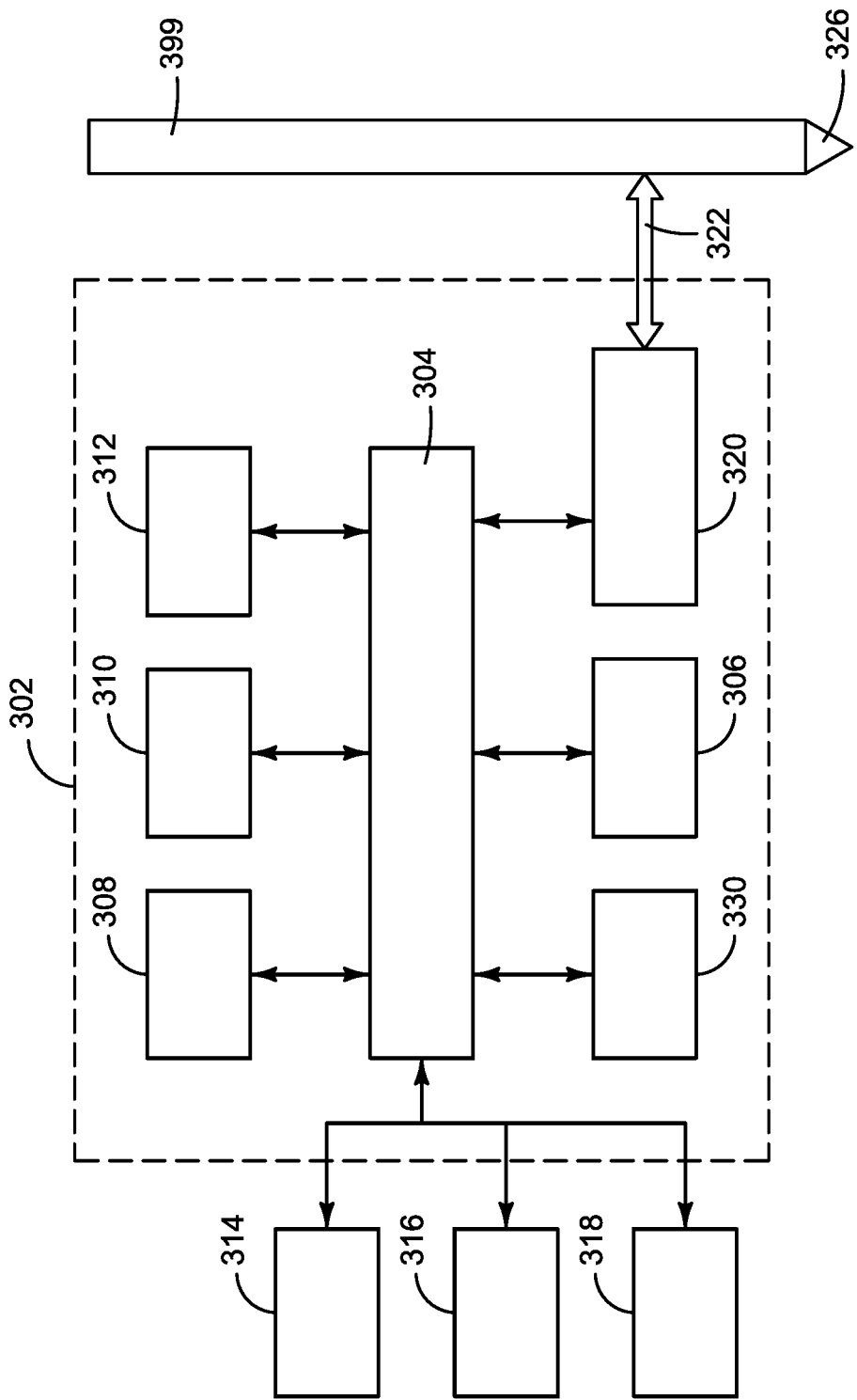
FIG. 8 is a schematic representation of an exemplary control system.
Figure 9:
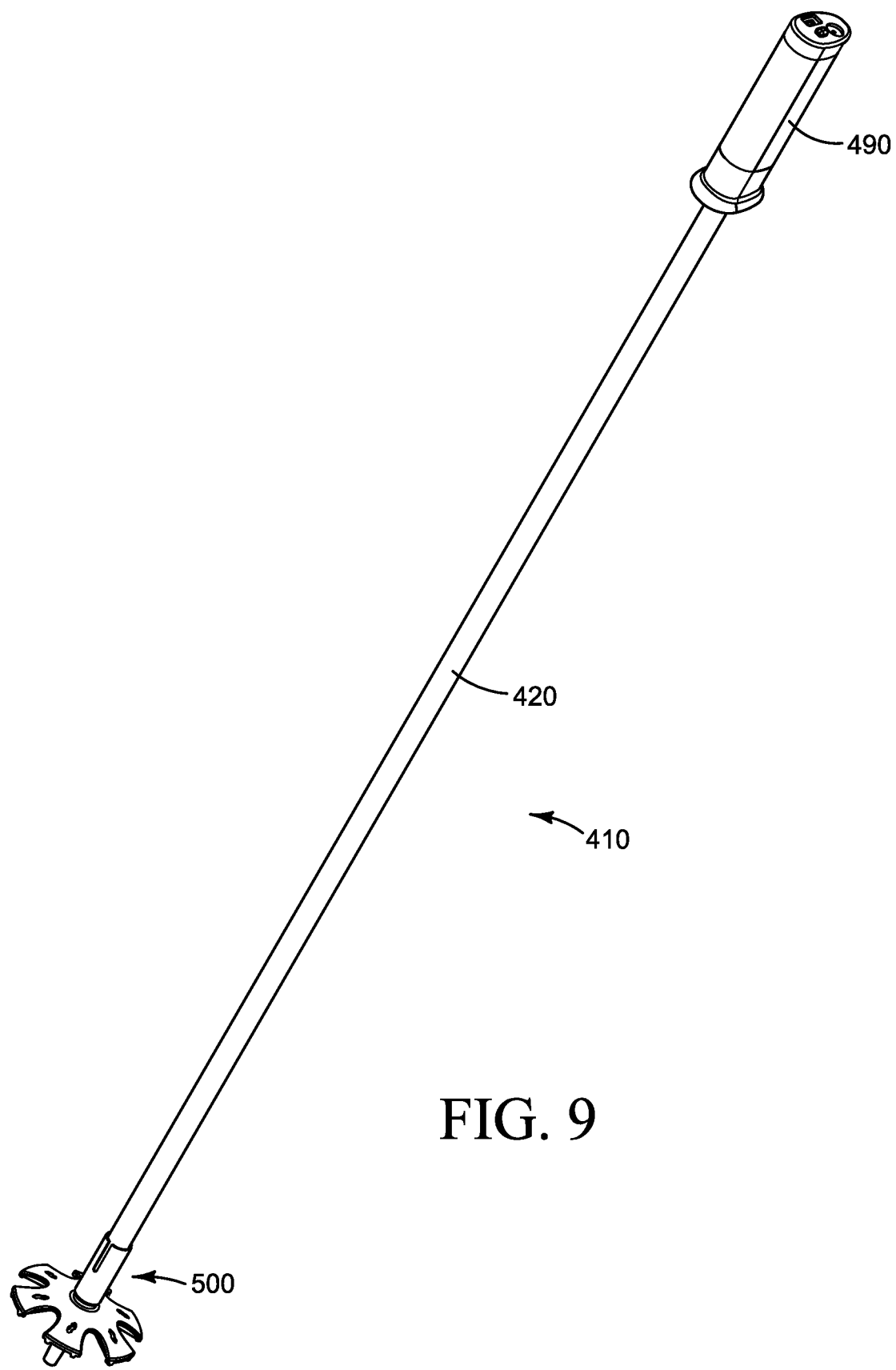
FIG. 9 is a perspective view of the third exemplary sensor system.

FIG. 8 illustrates an exemplary control system 302 upon which an exemplary sensor system may be implemented and/or utilized in connection with. The control system 302 includes a communication mechanism for to communicate information, and a processor 306 coupled with the communication mechanism to process the information. The control system 302 also includes a main memory 308, such as a random access memory (RAM) or other dynamic storage device (e.g., dynamic RAM (DRAM), static RAM (SRAM), synchronous DRAM (SDRAM), flash RAM), coupled to the communication mechanism to store information and instructions to be executed by processor 306. In addition, main memory 308 may be used to store temporary variables or other intermediate information during execution of instructions to be executed by processor 306. Control system 302 further includes a read only memory (ROM) 310 or other static storage device (e.g., programmable ROM (PROM), erasable PROM (EPROM), and electrically erasable PROM (EEPROM)) coupled to the communication mechanism to store static information and instructions for processor 306. A storage device 312, such as a magnetic disk or optical disk, may be provided to store information and instructions.

The control system 302 also includes input/output ports 330 to couple the control system 302 to external devices. Such coupling may include direct electrical connections, wireless connections, networked connections, etc., for implementing automatic control functions, remote control functions, etc.

The control system 302 performs a portion or all of the processing steps of the invention in response to processor 306 executing one or more sequences of one or more instructions contained in a memory, such as the main memory 308. Such instructions may be read into the main memory 308 from another computer readable medium, such as storage device 312. One or more processors in a multi-processing arrangement may also be employed to execute the sequences of instructions contained in main memory 308. In alternative embodiments, hard-wired circuitry may be used in place of or in combination with software instructions. Thus, embodiments are not limited to any specific combination of hardware circuitry and software.

As stated above, the control system 302 includes at least one computer readable medium or memory programmed according to the teachings of the invention and for containing data structures, tables, records, or other data described herein. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software to control the control system 302, to drive a device or devices for implementing the invention, and to enable the control system 302 to interact with a human user. Such software may include, but is not limited to, device drivers, operating systems, development tools, and applications software. Such computer readable media further includes the computer program product of the present invention to perform all or a portion (if processing is distributed) of the processing performed in implementing the invention.

The computer code devices of the present invention may be any interpreted or executable code mechanism, which includes but is not limited to scripts, interpreters, dynamic link libraries, Java classes, and complete executable programs. Moreover, parts of the processing of the present invention may be distributed for better performance, reliability, and/or cost.

The term "computer readable medium" as used herein refers to any medium that participates in providing instructions to processor 306 for execution. A computer readable medium may take many forms, including but not limited to, non-volatile media, volatile media, and transmission media. Non-volatile media includes, for example, optical, magnetic disks, and magneto-optical disks, such as storage device 312. Volatile media includes dynamic memory, such as main memory 308. Transmission media includes coaxial cables, copper wire and fiber optics, including the wires that comprise bus 304. Transmission media also may also take the form of acoustic or light waves, such as those generated during radio wave and infrared data communications.

Common forms of computer readable media include, for example, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), or any other optical medium, punch cards, paper tape, or other physical medium with patterns of holes, a carrier wave (described below), or any other medium from which a computer can read.

Various forms of computer readable media may be involved in carrying out one or more sequences of one or more instructions to processor 306 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to control system 302 may receive the data on the telephone line and use an infrared transmitter to convert the data to an infrared signal. An infrared detector coupled to bus 304 can receive the data carried in the infrared signal and place the data on bus 304. The bus 304 carries the data to main memory 308, from which processor 306 retrieves and executes the instructions. The instructions received by main memory 308 may optionally be stored on storage device 312 either before or after execution by processor 306.

The control system 302 also includes a communication interface 320 coupled to bus 304. Communication interface 320 provides a two-way data communication coupling to a network link 322 that may be connected to, for example, a probe. For example, communication interface 320 may be a wireless link, for instance a Bluetooth connection, implemented via the communication interface 320, wherein the communication interface 320 sends and receives electrical, electromagnetic or optical signals that carry digital data streams representing various types of information.

FIGS. 9 through 13 illustrate a third exemplary sensor system 410 for measuring the profile of a snowpack along a snowpack passage 4 (such as illustrated in FIG. 1) and assessing avalanche risk. The third exemplary sensor system 410 is similar to the first exemplary sensor system 10 illustrated in FIGS. 1 through 6 and described above, except as detailed below.

The third exemplary sensor system 410 includes a probe 420 that has an inner wall 423 and outer wall 424. The inner wall 423 and outer wall 424 extend from a first end 421 to a second end 422. The second end 422 comprises a probe tip 426 for insertion into a snowpack 2 (such as illustrated in FIG. 1). Preferably, the probe 420 is generally cylindrical in shape, such that the inner wall 423 and outer wall 424 form a cavity 427. Preferably, the cavity extends from the first end 421 to the second end 422, which allows components to be housed therein.

The first end 421 of the probe 420 comprises a handle portion 490. Preferably, the handle portion 490 comprises a handle body 491 defining a handle cavity 492 configured to receive therein the control system 480 and an energy storage system 485. Both the control system 480 and the energy storage system 485 are illustrated generally. Optionally, the control system 480 can be contained elsewhere, such as in an external electronic device 82, such as the one illustrated in FIG. 1. Likewise, the energy storage system 485 could be located elsewhere.

Figure 10:
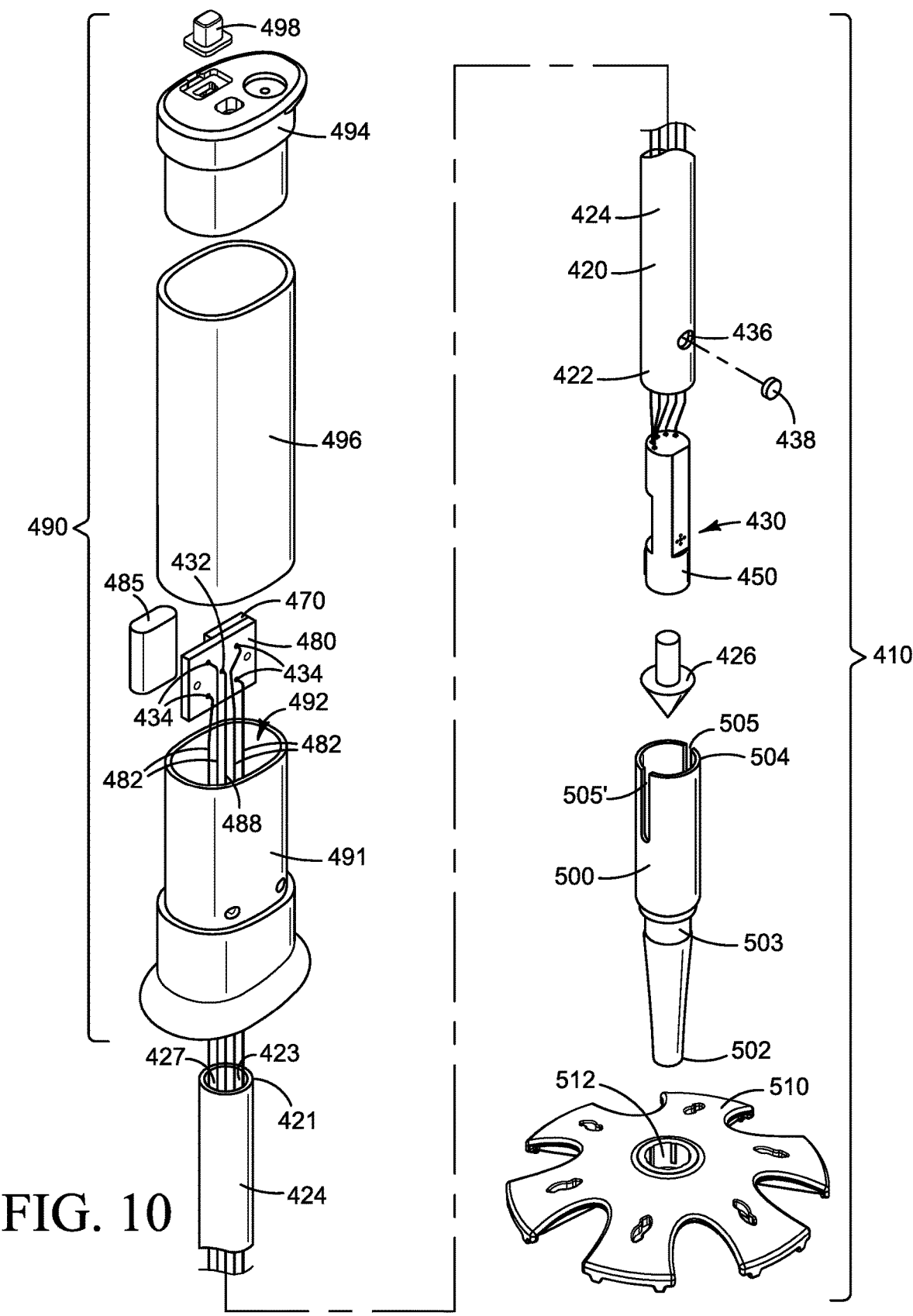
FIG. 10 is an exploded, perspective view of the third exemplary sensor system of FIG. 9.
Figure 11:
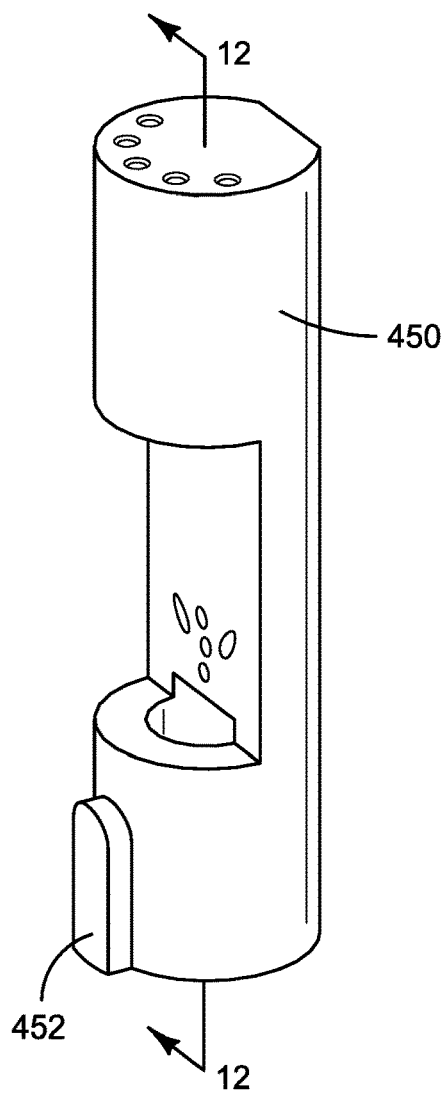
FIG. 11 is a perspective view of an exemplary sensor mount used with the third exemplary sensor system of FIG. 9.
Figure 12:
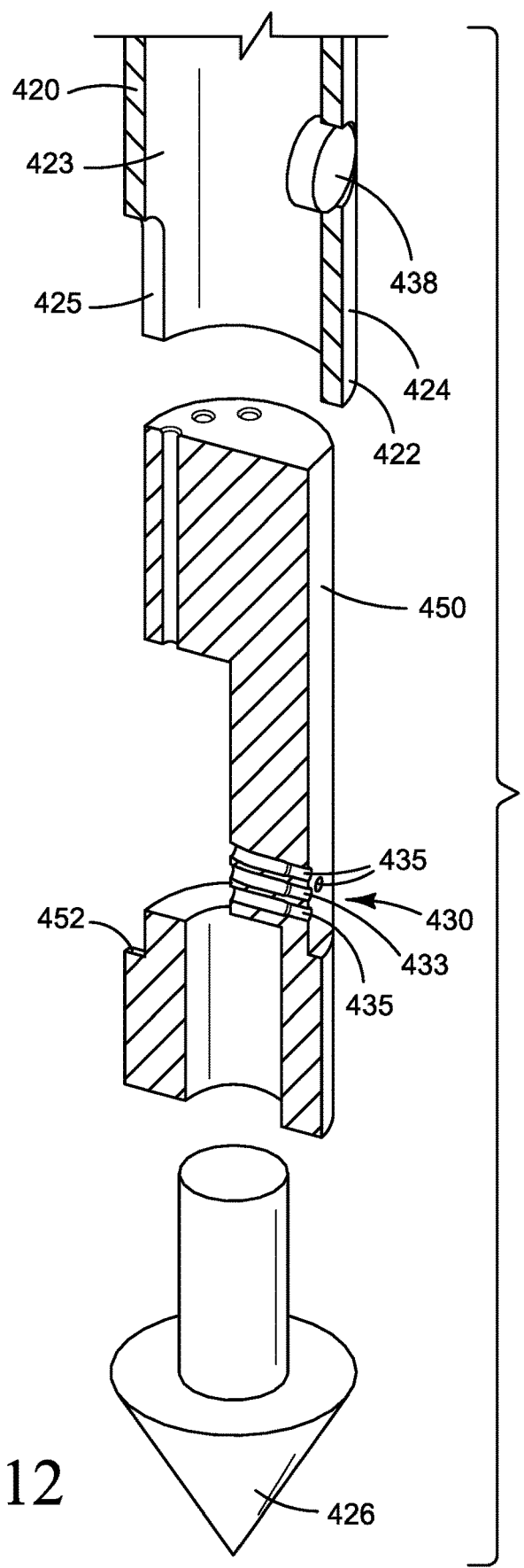
FIG. 12 is a partial, cross-sectional, perspective view of the third exemplary sensor system of FIG. 9.
Figure 13:
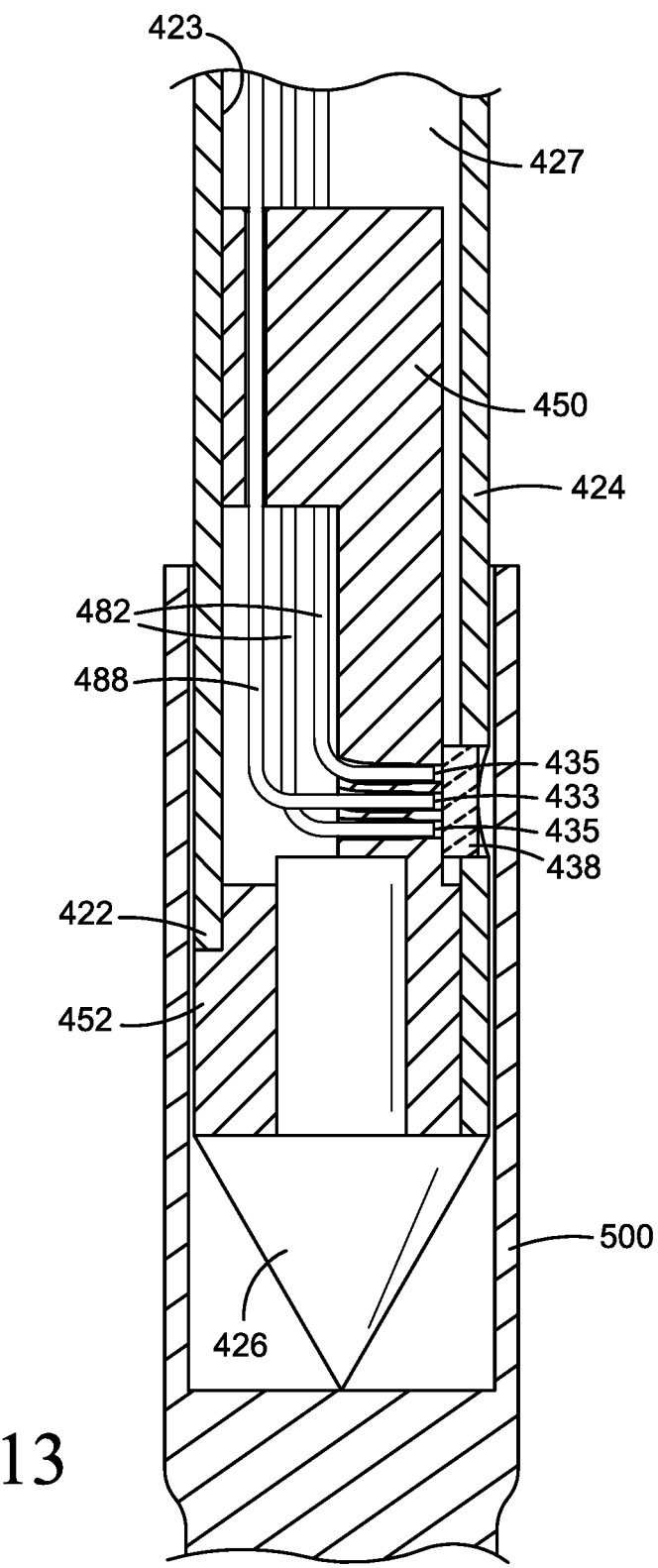
FIG. 13 is a partial, cross-sectional, side view of the third exemplary sensor system of FIG. 9.

The handle portion 490 serves as point for a user to grasp when he or she inserts the third exemplary sensor system 410 into a snowpack. Preferably, the handle portion 490 comprises a gripping portion 496 that gives the user extra stability when he or she exerts a downwards force upon the probe 420. An end cap 494 is illustrated in FIG. 10. The end cap 494 is for covering the end of the handle portion 490. Illustrated in the end cap 494 is a button 498 for providing user input into the operation of the sensor system 410. For instance, the button 498 could be utilized to turn the sensor system 410 on or off, or the button 498 turn the sensor system 410 on while depressed, and turn the sensor system 410 off when not depressed.

The third exemplary sensor system 410 further comprises a speed sensor for sensing speed at which the probe 420 is inserted into the snowpack. In the third exemplary sensor system 410, the speed sensor comprises a barometer 470. Preferably, the barometer is a high resolution barometer configured for taking barometric pressure measurements. Because air pressure is a function of the air column height, the barometer 470 can be used to sense small, relative changes in air pressure to account for change in the position of the probe 420. The barometer 470 is preferably located in the handle cavity 492.

As the user inserts the probe 420 into the snowpack, the air pressure increases slightly. This air pressure change is sensed by the barometer 470, and an air pressure signal is generated and is sent to the control system 480. Using the using physical properties of the air and gravity, the displacement of the handle portion 490 from the original position of the handle portion 490 can be calculated by the processor of the control system 480, thereby sensing the speed at which the probe 420 moved through the snowpack and generating a second output signal.

Alternatively, the second output signal can be calculated using another process. For instance, an infra-red light photoemitter could shine down from the handle and reflect off a moving basket that contacts the upper surface of the snowpack and slides along the probe as the probe is inserted into the snowpack. The reflected light would then be received by a photodetector to generate a signal representing the relative movement of the probe. A skilled artisan will be able to select an appropriate manner of generating a second output signal relating to movement in a particular embodiment based on various considerations, including the intended use of the sensory system, the intended arena within which the sensory system will be used, and the equipment and/or accessories with which the sensory system is intended to be used, among other considerations.

The probe tip 426 is the leading edge of the probe 420, and is preferably configured for minimal resistance when the probe tip 426 penetrates a snowpack. The probe tip 426 is preferably an aluminum cylinder that is glued, attached by a mechanical fastener, or is press-fit into the second end 422 of the probe 420, however a skilled artisan will be able to select an appropriate structure and material for the probe 420 and probe tip 426, as well as how the probe tip 426 is attached to the second end 422 of the probe 420, in a particular embodiment based on various considerations, including the intended use of the probe 420 and probe tip 426, the intended arena within which the probe 420 and probe tip 426 will be used, and the equipment and/or accessories with which the probe 420 and probe tip 426 are intended to be used, among other considerations.

Preferably, the probe tip 426 has a generally conical shape, such as is illustrated in these figures. Alternatively, the shape of the probe tip 426 can be altered without any change in functionality, perhaps even performance enhancing benefits, for instance through the use of a sharpened or rectangular tip has help to reduce the alteration of the snowpack as the probe penetrates.

The third exemplary sensor system 410 further comprises a sensor set 430 configured to detect variations in the characteristics of a snowpack and to provide a corresponding data output to a processor in the control system 480 which calculates a snowpack profile. In the third exemplary sensor system 410, the sensor set 430 comprises one photoemitter 432 and four photodetectors 434. In other exemplary sensor systems, the sensor set will comprise one or more photoemitters, and one or more photodetectors. Further, in other exemplary sensor systems, more than one sensor set.

The photoemitter 432 is configured for emitting a light signal towards and into the snowpack, and the photodetectors 434 are configured to detect the intensity of the light signal reflected back from the snowpack in a snowpack passage and to output a first output signal related to light intensity detected by the photodetectors 434.

In third exemplary sensor system 410, the photoemitter 432 is located on the control system 480, and emitted light is transferred to a photoemitter port 433 located in the sensor set 430 via an optical fiber 488. Further, the photoemitters 434 are also located on the control system 480, and received light is transferred from photodectector ports 435 to the photodetectors via optical fibers 482.

Preferably, the photoemitter 432 emits infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the photoemitter 432 could emit visible and/or ultraviolet light in addition to, or instead of, infrared light.

The photodetectors 434 are configured for sensing light emitted from the photoemitter 432 which has reflected off a snowpack in a snowpack passage. In that the preferred photoemitter 432 emits infrared light, the photodetectors 434 are configured for sensing infrared light. While infrared light is the preferred light, a skilled artisan will be able to select an appropriate light in a particular embodiment based on various considerations, including the intended use of the sensor system, the intended arena within which the sensor system will be used, and the equipment and/or accessories with which the sensor system is intended to be used, among other considerations. For instance, the photodetectors 434 could detect visible and/or ultraviolet light in addition to, or instead of, infrared light.

When the third exemplary sensor system 410 is inserted into the snowpack and moved along a snowpack passage, the light signal is emitted into the snowpack, and the photodetectors 434 detects the light signal.

The photodetectors 434 generates a first output signal related to the intensity of the light signal reflected off the snowpack in the snowpack passage and back to the photodetectors 434. This first output signal is then transferred to the processor of the control system 480. The sensor set 430 is configured to detect variations in the characteristics of a snowpack and to provide corresponding data output (the first output signal) to the processor of the control system 480. Once the processor receives the first output signal, the first output signal can be processed into a snowpack profile that is presented to a user. In other examples, other characteristics of a snowpack could be utilized. For instance, temperature, snow water equivalent, snow density, grain types, albedo, etc.

The sensor set 430 is mounted or otherwise attached to the probe 420. In the exemplary sensor system 410 illustrated in these Figures, the probe 420 comprises a sensor mount 450 to which the sensor set 430 can be mounted. The sensor mount 450 is attached to the inner wall 423 of the probe 420, adjacent the probe tip 426. Alternatively, the sensor mount 450 could be attached to the inner wall 423 of the probe 420 not adjacent the probe tip 426. The sensor mount 450 is for holding the sensor set 430. Preferably, the sensor mount 450 is glued into the inner wall 423. Alternatively, other manners of connecting the sensor mount to the probe could be utilized Preferably, the sensor mount 450 includes an alignment portion 452, and the probe 420 preferably also includes an alignment portion 425. The alignment portion 452 and alignment portion 425 for aligning the sensor mount 450 in the probe 420.

Also adjacent the probe tip 426 is a sensor viewport 436. The sensor viewport 436 extends through both the inner wall 223 and the outer wall 224, allowing the photoemitter 432 to emit a light signal in a first direction. Additionally, the sensor viewport 436 allows the photodetector 434 to receive deflected light traveling in a second direction.

Preferably, the sensor viewport 436 is covered by a sensor viewport cover 438. This viewport cover 438 allows for the transmission of light therethrough, and is made of any plastic that allows light to freely pass therethrough. Alternatively, the sensor viewport 436 can be made of a light filtering material, for instance acrylic plastic. Such a material is incorporated to accommodate filtering undesired wavelengths of light.

The control system 480 is configured to receive data corresponding to the output signals. In this exemplary sensor system 410, the control system 480 is preferably located within the handle cavity 492 of the handle body 491 of the handle 490.

In the exemplary sensory system 410 the processor of the control system 480 preferably executes at least three algorithms to determine the snowpack profile.

The first algorithm processes the first output signal to calculate a light intensity profile.

The second algorithm processes the second output signal relative to the first output signal to calculate a speed profile. The speed profile represents the relative movement of the probe 420 as it is moved along the snowpack 2.

The third algorithm processes the light intensity profile in view of the speed profile to create the snowpack profile.

Preferably, the snowpack profile is displayed on a display 90 for the user to view. Preferably, the display 90 is located external the probe 420 in a device such as a computer, PDA, or cellular phone. Alternatively, the display 90 could be located on the probe 420 of the third exemplary sensor system 410 such that a user can readily view it. Again, a skilled artisan will be able to select an appropriate structure and material for the display 90 in a particular embodiment based on various considerations, including the intended use of the display 90, the intended arena within which the display 90 will be used, and the equipment and/or accessories with which the display 90 is intended to be used, among other considerations.

As the probe 420 is inserted into the snowpack 2 in a generally linear manner, the snowpack properties are measured transversely. By measuring transversely, more accurate measurements can be achieved by measuring the undisturbed snow adjacent to the path of the probe (along a snowpack passage). This is opposed to measuring oncoming, damaged snow, damaged by the probe 420 sliding through the snowpack passage 4.

By measuring the amount of light that is reflected off, or transmitted through, a snowpack 2 in a snowpack passage 4, the third exemplary sensor system 410 can calculate a snowpack profile. Further, the configuration of the photoemitter 432 can be used to measure snow properties in-situ with minimal impact on the snow structure. The third exemplary sensor system 410 thus measures the albedo, refraction, and transparency of the layers in the snowpack along the snowpack passage, to which properties of the snowpack can be correlated.

The third exemplary sensor system 410 can send measurements to a mobile device via a wireless transmission technology such as Bluetooth low energy. The mobile device can then process the data and upload it directly to a server, which hosts a web platform for users to view the data.

When not in use, a tip cover 500 can be placed over the probe tip 426 to protect the probe tip 426 from damage when not in use. The tip cover 500 comprising a tip cover end 502 for insertion into a snowpack surface, and a probe receiver end 504 for receiving the probe tip 426 therein. Preferably, the tip cover 500 covers one or more of the sensor sets and protects them from damage.

The tip cover 500 illustrated in the drawings comprising a plurality of grooves (505, 505') defined in the probe receiver end 504 for enabling the tip cover 500 to be held onto the tip end of the probe 420 via a compression fit. Other types and manners of connecting the tip cover 500 to the probe 420 are possible and a skilled artisan will be able to select an appropriate structure and material for the connecting the tip cover 500 to the probe 420 in a particular embodiment based on various considerations, including the intended use of the sensor system, the intended arena within which the sensor system will be used, and the equipment and/or accessories with which the sensor system is intended to be used, among other considerations.

The illustrated tip cover 500 having a basket 510 for limiting the insertion of the probe tip 426 into the snowpack 2 when the embodiments of the exemplary sensor systems are not in use. The tip cover 500 may or may not be present. The basket 510 illustrated in the Figures is removable, having a orifice passage 512 defined therethrough able to receive the tip cover end 502 therethrough, the basket 510 sliding onto the tip cover 500, with the orifice passage 512 being received in a basket groove 503 defined in the tip cover. Alternatively, the basket 510 could slide onto the probe 420 without the tip cover 500 protecting the probe tip 426. Alternatively, the basket 510 could comprise a sensor cover (not illustrated) for protecting the sensor set(s).

In a fourth exemplary sensor system for measuring the profile of a snowpack along a snowpack passage, the sensor system comprises a probe and a handheld computing device. The probe comprises at least one first sensor set, at least one second sensor set, and a transmitter. The first sensor set comprises at least one first photoemitter and at least one first photodetector. The at least one first photoemitter is for emitting a first light signal towards the snowpack passage. The at least one first photodetector is for detecting the intensities of the first light signal reflected back from the snowpack passage.

The first sensor set generates a first output signal related to light intensity detected by the at least one first photodetector. The second sensor set comprises at least one second photoemitter and at least one second photodetector. The at least one second photoemitter is for emitting a second light signal towards the snowpack passage. The at least one second photodetector is for detecting the intensities of the second light signal reflected back from the snowpack passage. The second sensor set generates a second output signal related to light intensity detected by the least one second photodetector. The transmitter is for transmitting the first output signal and the second output signal.

The handheld computing device comprises a receiver for receiving the first output signal and the second output signal. The handheld computing device comprises at least one processor. The processor is for implementing processor functions in response to receiving the first output signal and the second output signal. The processor functions include: executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile. Preferably, the snowpack profile is displayed to a user via a user interface. Alternatively, the user interface comprises a digital screen, and the snowpack profile is displayed to the user via the digital screen.

A fifth exemplary sensor system for measuring the profile of a snowpack along a snowpack passage, comprises a probe, and a handheld computing device. The probe comprises at least one first sensor set, at least one second sensor set, and a transmitter.

The first sensor set comprises at least one first photoemitter and at least one first photodetector. The at least one first photoemitter is for emitting a first light signal towards the snowpack passage, and the at least one first photodetector is for detecting the intensities of the first light signal reflected back from the snowpack passage. The first sensor set generates a first output signal related to light intensity detected by the at least one first photodetector.

The second sensor set comprises at least one second photoemitter and at least one second photodetector. The at least one second photoemitter is for emitting a second light signal towards the snowpack passage. The at least one second photodetector is for detecting the intensities of the second light signal reflected back from the snowpack passage. The second sensor set is for generating a second output signal related to light intensity detected by the at least one second photodetector. The transmitter is for transmitting the first output signal and the second output signal.

The handheld computing device comprises a receiver for receiving the first output signal and the second output signal. The handheld computing device comprises at least one processor. The processor is for implementing processor functions in response to receiving the first output signal and the second output signal. The processor functions including: executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile. The snowpack profile is displayed to a user via a user interface comprises a digital screen.

In another exemplary sensor system (not illustrated in the drawings), the sensor set (or sensor sets) could be located in one or more arrays positioned around the probe outer wall. By using an array(s) of sensors arranged cylindrically, the sensor set(s) would cover all 360 degrees of the snowpack. Any number of sensor sets could be used in a cylindrical array covering up to 360 degrees around the body of the probe.

In another exemplary sensor system (not illustrated in the drawings), the sensor sets are placed at least 90 degrees radially from one another around the body of the probe.

In another exemplary sensor system (not illustrated in the drawings) the probe comprises a plurality of collapsible sections configured for allowing the probe can be stored in a compact form.

In another exemplary sensor system (not illustrated in the drawings), the sensor system for measuring the snowpack profile further comprises an accelerometer to assist in signal correction. Specifically, the accelerometer measures any change in velocity, as the probe is being inserted into a snowpack, and transmits the change to the processor. The processor, in turn, uses this data in processing any of the at least three algorithms. For example, in processing the third algorithm, the first sensor set and second sensor set measure the time it takes both sensor sets to pass a single point in the snowpack. Because the speed of the probe is known, the algorithm uses speed and time to calculate distance. The accuracy of this algorithm is improved through the use of an accelerometer. The accelerometer is able to report, to the processor, any subtle changes in velocity. Such changes can be caused by any impediments in the snowpack passage. By using the true velocity of the probe in its calculation, the processor is able to provide a more-accurate snow profile.

The foregoing detailed description provides exemplary embodiments of the invention and includes the best mode for practicing the invention. The description and illustration of these embodiments is intended only to provide examples of the invention, and not to limit the scope of the invention, or its protection, in any manner.

What is claimed is:

1. A sensor system for measuring the profile of a snowpack along a snowpack passage, said sensor system comprising:
  a probe and at least one processor;
    said probe comprising a probe tip for insertion into said snowpack;

said probe comprising at least one first sensor set, said
   first sensor set comprising at least one first photoemitter
   and at least one first photodetector, said at least one first
   photoemitter for emitting a first light signal towards
   and into said snowpack passage at a first sensor set port,
   said at least one first photodetector at a second sensor
   set port for detecting the intensities of said first light
   signal reflected back from said snowpack passage, said
   first sensor set generating a first output signal related to
   light intensity detected by said at least one first pho-
   todetector, said probe generating a second output signal
   related to the speed at which the probe moved through
   the snowpack; and
said at least one processor for implementing processor
   functions in response to receiving said first output
   signal and said second output signal, said processor
   functions including:
executing an algorithm to process the first output signal to
   calculate a light intensity profile,
executing an algorithm to process the second output
   signal relative to the first output signal to calculate a
   speed profile representing the relative movement of the
   probe as it was moved along the snowpack passage, and
executing an algorithm to process the light intensity
   profile in view of the speed profile to calculate a
   snowpack profile.

2. The sensor system of claim 1, wherein said at least one first photoemitter emits infrared light, and wherein said at least one first photodetector detects infrared light.

3. The sensor system of claim 1, wherein said probe further comprises a barometer, and wherein the second output signal is generated by said barometer.

4. The sensor system of claim 3, wherein said barometer generates said second output signal by sensing relative changes in air pressure to account for change in the position of the probe.

5. The sensor system of claim 1, wherein:
said first sensor set port and said second sensor set port are located proximal to said probe tip;
said at least one first photoemitter and said at least one first photodetector of said at least one first sensor set is located distally from said probe tip;
said at least one sensor set further comprises at least one first optical fiber for transferring light from said at least one first photoemitter to at least one photoemitter port, and at least one second optical fiber for transferring light from at least one photodetector port to said at least one first photodetector;
wherein said first sensor set port comprises said at least one photoemitter port; and
wherein said second sensor set port comprises said at least one photodetector port.

6. The sensor system of claim 1, further comprising a second sensor set, said second sensor set comprising at least one second photoemitter and at least one second photodetector, said at least one second photoemitter for emitting a second light signal towards said snowpack passage, said at least one second photodetector for detecting the intensities of said second light signal reflected back from said snowpack passage, said second sensor set generating a second output signal related to light intensity detected by said at least one second photodetector.

7. The sensor system of claim 6, wherein said at least one first photoemitter and said at least one second photoemitter emit infrared light; and wherein said at least one first photodetector and said at least one second photodetector detect infrared light.

8. The sensor system of claim 7, wherein said at least one processor for further implementing processor functions in response to receiving said second output signal.

9. The sensor system of claim 1, wherein the number of first photoemitters is one, and the number of first photodetectors is four.

10. The sensor system of claim 1, wherein the probe defines a sensor viewport for receiving the first sensor set port and said second sensor set port, and wherein said probe further comprises a sensor viewport cover for covering said sensor viewport.

11. The sensor system of claim 10, wherein said sensor viewport cover is covered with hydrophobic coating.

12. The sensor system of claim 1, wherein said sensor system further comprises a transmitter for transmitting said first output signal and said second output signal to a receiver integrated into a handheld computing device comprising said processor.

13. The sensor system of claim 12, wherein said handheld computing device comprises a digital screen, and wherein said snowpack profile is displayed to a user via said digital screen.

14. The sensor system of claim 1, wherein said sensor system further comprises a transmitter for transmitting said first output signal and said second output signal to a receiver integrated into a handheld computing device comprising said processor, wherein said handheld computing device comprises a digital screen, and wherein said snowpack profile is displayed to a user via said digital screen.

15. The sensor system of claim 1, wherein said probe comprises a first end extending to a second end, said first end comprising a handle, and said second end comprising a tip configured for insertion into snowpack.

16. The sensor system of claim 15, wherein said probe comprises a hollow pole, and wherein said hollow pole comprises a plurality of connected segments which can be disconnected from one another to make the pole collapsible.

17. The sensor system of 16, wherein said plurality of connected segments are held in a connected state through use of a magnetic connection, and wherein said sensor further comprises a basket for limiting the insertion of the probe tip into the snowpack, wherein said basket attaches to said pole via a magnetic connection.

18. The sensor system of claim 1, wherein:
said at least one first photoemitter emits infrared light, and wherein said at least one first photodetector detects infrared light;
said first sensor set port and said second sensor set port are located proximal to said probe tip;
said at least one first photoemitter and said at least one first photodetector of said at least one sensor set is located distally from said probe tip;
said at least one sensor set further comprises at least one first optical fiber for transferring light from said at least one first photoemitter to at least one photoemitter port, and at least one second optical fiber for transferring light from at least one photodetector port to said at least one first photodetector;
wherein said first sensor set port comprises said at least one photoemitter port; and
wherein said second sensor set port comprises said at least one photodetector port.

19. A sensor system for measuring the profile of a snowpack along a snowpack passage, said sensor system comprising:
a probe and at least one processor;

said probe comprising a probe tip for insertion into said snowpack;

said probe comprising at least one first sensor set, said first sensor set comprising at least one first photoemitter and at least one first photodetector, said at least one first photoemitter for emitting a first light signal towards and into said snowpack passage at a first sensor set port, wherein said at least one first photoemitter emits infrared light, wherein said at least one first photodetector detects infrared light, said at least one first photodetector at a second sensor set port for detecting the intensities of said first light signal reflected back from said snowpack passage, said first sensor set generating a first output signal related to light intensity detected by said at least one first photodetector, said probe generating a second output signal related to the speed at which the probe moved through the snowpack, wherein said probe further comprises a barometer, and wherein the second output signal is generated by said barometer; and said at least one processor for implementing processor functions in response to receiving said first output signal and said second output signal, said processor functions including:

executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile.

20. A sensor system for measuring the profile of a snowpack along a snowpack passage, said sensor system comprising:

a probe and at least one processor;

said probe comprising a probe tip for insertion into said snowpack;

said probe comprising at least one first sensor set, said first sensor set comprising at least one first photoemitter and at least one first photodetector, said at least one first photoemitter for emitting a first light signal towards and into said snowpack passage at a first sensor set port, wherein said at least one first photoemitter emits infrared light, wherein said at least one first photodetector detects infrared light, said at least one first photodetector at a second sensor set port for detecting the intensities of said first light signal reflected back from said snowpack passage, said first sensor set port and said second sensor set port are located proximal to said probe tip, wherein said at least one first photoemitter and said at least one first photodetector of said at least one sensor set is located distally from said probe tip, said first sensor set generating a first output signal related to light intensity detected by said at least one first photodetector, said probe generating a second output signal related to the speed at which the probe moved through the snowpack, wherein said probe further comprises a barometer, and wherein the second output signal is generated by said barometer; and said at least one processor for implementing processor functions in response to receiving said first output signal and said second output signal, said processor functions including:

executing an algorithm to process the first output signal to calculate a light intensity profile, executing an algorithm to process the second output signal relative to the first output signal to calculate a speed profile representing the relative movement of the probe as it was moved along the snowpack passage, and executing an algorithm to process the light intensity profile in view of the speed profile to calculate a snowpack profile;

wherein said at least one sensor set further comprises at least one first optical fiber for transferring light from said at least one first photoemitter to at least one photoemitter port, and at least one second optical fiber for transferring light from at least one photodetector port to said at least one first photodetector, wherein said first sensor set port comprises said at least one photoemitter port, and wherein said second sensor set port comprises said at least one photodetector port.

* * * * *